United States Patent [19]
Bell et al.

[11] Patent Number: 5,392,910
[45] Date of Patent: Feb. 28, 1995

[54] PACKAGE FOR A DEVICE HAVING A SHARP CUTTING EDGE

[75] Inventors: Bruce M. Bell, Simpsonville; Steven W. Butler, Spartanburg, both of S.C.

[73] Assignee: Transidyne General Corporation, Spartanburg, S.C.

[21] Appl. No.: 278,131

[22] Filed: Jul. 21, 1994

[51] Int. Cl.⁶ ............................................. B65D 81/00
[52] U.S. Cl. ................................. 206/363; 206/467; 206/524.3
[58] Field of Search .............. 206/349, 363, 438, 461, 206/467, 469, 523, 524.3

[56] References Cited

U.S. PATENT DOCUMENTS

| | | |
|---|---|---|
| 1,733,971 | 10/1929 | Kremer . |
| 3,082,862 | 3/1963 | Nicholson et al. . |
| 3,891,088 | 6/1975 | Huebner .................. 206/349 |
| 4,322,001 | 3/1982 | Hurley . |
| 4,344,532 | 8/1982 | Eldridge, Jr. et al. ......... 206/363 X |
| 4,511,035 | 4/1985 | Alpern ..................... 206/363 |
| 4,750,619 | 6/1988 | Cohen et al. .............. 206/363 X |
| 5,213,207 | 5/1993 | Konev .................... 206/349 X |
| 5,284,244 | 2/1994 | O'Toole et al. ............ 206/467 X |

FOREIGN PATENT DOCUMENTS 169447A 1/1986 European Pat. Off. .
2200894A 8/1988 United Kingdom .

Primary Examiner—Jacob K. Ackun, Jr.
Attorney, Agent, or Firm—Watson, Cole, Grindle & Watson

[57] ABSTRACT

A package for a device having a sharp cutting edge, such as a bone saw, includes a tray having a bottom surface, a top surface and side walls. The side walls are connected between the bottom surface and the top surface. The top surface includes an upwardly facing central recessed portion for engaging a device such as a bone saw. The tray defines a downwardly facing recessed area adjacent the central portion. A protective strip of cushioning material is disposed within the downwardly facing recessed area and extends above and below the central portion. The protective strip prevents the device from engaging the side walls and is formed of a plastic sponge material which is soft, resilient and tear-resistant. A cover secured to the bottom surface of the tray retains the protective strip in operative position.

20 Claims, 1 Drawing Sheet

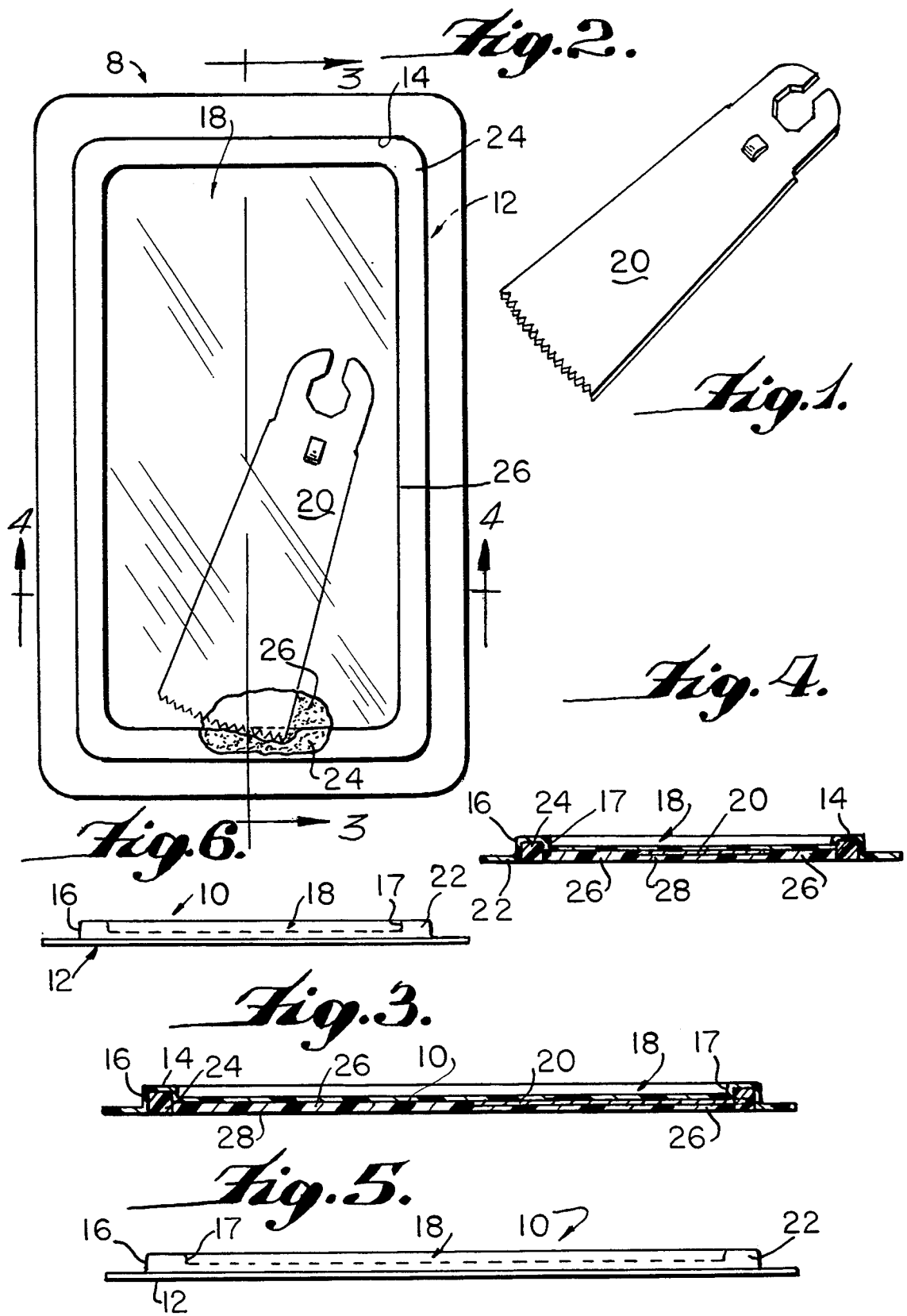

PACKAGE FOR A DEVICE HAVING A SHARP CUTTING EDGE

FIELD OF THE INVENTION

The present invention relates to a package for a device having sharp cutting edge. More specifically, the present invention relates to a protective and sterile package for transporting and storing a bone saw.

BACKGROUND OF THE INVENTION

It is well known that devices having a sharp cutting edge must be packaged in a manner which protects the edge. A need exists for a package which protects the sharp cutting edge of a surgical instrument, particularly a bone saw.

Bone saws must remain sterile until just prior to use. They must also be free of contaminating materials such as flecking from packaging material such as plastic, foam and sponge. Because it is desirable to provide a single package which can be used for various sized devices, there may be some room for movement of relatively small devices in the package. A smaller bone saw may shift within a relatively larger package and it is possible for the sharp cutting edge of the saw to impact a portion of the package, for example, an inner side wall.

The sharp cutting edge of a bone saw such as the one shown in FIG. 1 has a plurality of teeth in a row which alternately extend in opposite directions laterally of the plane of the saw blade. The design provides a saw which can readily scrape flecking from the surface of plastic packaging it impacts. Polyethylene terephthalate (PET) is one particularly common plastic used to mold packages for a huge variety of devices and objects but which can fleck-off when impacted by a sharp cutting edge.

When devices having sharp cutting edges are packaged, foam and sponge materials are also often used and may act to snugly bias the device within the package. Although the sponge and foam materials can cushion the impact of a sharp cutting edge, these types of conventional packing materials can also fleck-off when impacted by a sharp cutting edge, resulting in contaminating particles. When sterile devices are packaged, it is particularly important to provide a cushioning material which will not fleck upon impact with a sharp cutting edge.

SUMMARY OF THE INVENTION

It is an object of the present invention to provide a package which can hold a device having a sharp cutting edge and which can protect and keep the edge sterile during transportation and storage. More particularly, it is an object of the present invention to provide a bone saw package which can hold a variety of bone saw sizes and which protects the sharp cutting edge in a sterile manner.

The package of the present invention comprises a tray having a bottom surface, a top surface and a side wall. The side wall is connected between the top and bottom surfaces of the tray. The top surface includes an upwardly facing central recessed portion for engaging a device having a sharp cutting edge, such as a bone saw. The tray defines a downwardly facing recessed area adjacent the central portion. A protective strip of cushioning material is disposed within the downwardly facing recessed area and extends above and below the central portion. The protective strip prevents the device from engaging the side walls and is formed of a plastic sponge material which is soft, resilient and tear-resistant. A support pad is also provided to bias the device toward the central recessed portion. A cover secured to the bottom surface of the tray retains the protective strip and support pad in operative position.

BRIEF DESCRIPTION OF THE DRAWINGS

The invention may be more fully understood with reference to the accompanying drawings, wherein FIG. 1 is a perspective view of a bone saw of the prior art;

FIG. 2 is a top view of a package according to the present invention having a bone saw disposed therein;

FIG. 3 is a partial cross-sectional view of the package shown in FIG. 2, taken along line 3—3;

FIG. 4 is a cross-sectional view of the package shown in FIG. 2, taken along line 4—4;

FIG. 5 is a side view of a tray of a package according to the present invention; and FIG. 6 is an end view of a tray of a package according to the present invention.

DETAILED DESCRIPTION OF THE INVENTION

A package according to an embodiment of the present invention is shown in FIGS. 2-4. The package 8 comprises a tray 10, which is best seen FIGS. 5 and 6. The tray 10 has a bottom surface 12, a top surface 14, and a side wall 16. The side wall 16 connects the top surface 14 and the bottom surface 12 of the tray. The top surface 14 includes an upwardly facing central recessed portion 18 for engaging a device having a sharp cutting edge, such as a bone saw 20. The tray defines a downwardly facing recessed area 22 adjacent the central recessed portion 18 and defined by side wall 17. In the rectangular embodiment illustrated, the side walls actually comprise a pair of longitudinal side walls having opposite ends thereof connected by end side walls.

A protective strip 24 of cushioning material is disposed within the downwardly facing recessed area 22 and extends above and below the central recessed portion 18 (FIGS. 2-4). The protective strip 24 prevents the device 20 from engaging the side wall 16 and is formed of a plastic sponge material which is soft, resilient and tear-resistant. A support pad 26 is also provided to bias the device 20 toward the central recessed portion 18. A cover 28 secured to the bottom surface 12 of the tray 10 retains the protective strip 24 and support pad 26 in operative position.

In the embodiment shown, the downwardly facing recessed area 22 surrounds the central recessed portion 18. The protective strip 24 is complementary in configuration to the downwardly facing recessed area 22. Also, the support pad 26 is surrounded by the protective strip 24. The protective strip and the support pad also have thicknesses which enable them to be flush with one another on the side of each which faces the cover 28, when in their operative positions. Preferably, the support pad 26 contacts the tray 10 on its top side in all but the area which contacts the bone saw.

Due to the spongy nature of the support pad, devices of different thicknesses may fit into the package of the present invention. As shown in FIGS. 2-4, the portion of the support pad supporting the device will be compressed when the cover is secured to the tray. The compressed portion of the support pad material biases the device against the tray. According to the present invention, a single size tray can hold a variety of sizes of devices such as bone saws or scapels.

According to a more general embodiment of the present invention, the package comprises a tray which includes a central portion and a recessed area adjacent to the central portion to define an interior space within the tray. A device having a sharp cutting edge is disposed within the space and is in contact with the central portion. Protective means such as a sponge strip is disposed within the recessed area for preventing the device from engaging any portion of the tray other than the central portion.

The tray may comprise almost any transparent plastic material and only need be a few mils thick. Polyethylene terephthalate is one preferred plastic material for the tray as it is transparent, easily molded, strong, durable and inexpensive. Many other plastic materials may be used for the tray. One particularly suitable plastic is PETG copolyester rigid film available as KLÖCKNER PENTAMED® 8G1 from Klöckner Pentaplast of America, Inc., Gordonsville, Va.

The protective strip and the support pad may be made from a single type of spongy material, although they do not have to be. The protective strip is preferably made of a plastic sponge material which is soft, resilient and tear-resistant. One such material is polyester foam grade 5210 AXXX available in precut shapes from Foamade Industries, Detroit, Mich. The protective strip has a thickness sufficient for it extend above and below the central portion of the tray for preventing a device having a sharp cutting edge from engaging the side wall. The support pad may likewise be made out of the same or similar material but is not as thick as the protective strip.

The cover may be made of a paper material which is plastic-coated, or of a plastic sheet-like material. One particular material which does not tear easily and is suitable for the cover is TYVEK®, a plastic coated paper stock available form, e.g., Paper Manufacturing Company, Philadelphia, Pa.

The cover is provided with a heat-sensitive adhesive which is activated to heat-seal the cover to the bottom surface of the tray. At least a small portion of the outer periphery of the cover is not sealed to the bottom surface, thus providing the cover with a tab which can be gripped to initiate separating the cover from the tray. In the embodiment shown in FIGS. 2-4, the cover is heat-sealed to the bottom surface of the tray but is not sealed to either the support pad or the protective strip.

After the cover has been sealed to the bottom surface of the tray, the entire package can be subjected to gamma irradiation to sterilize the device packaged therein.

Although a rectangular package configuration is shown in the drawings, it is to be understood that equivalent packages having other shapes and configurations such as square, circular, triangular, oval, etc. are also within the scope of the present invention. When a circular recess is provided, for example, the recess is defined by first and second side walls rather than by a pair of side walls connected at opposite ends thereof by end side walls.

Although the present invention has been described in connection with preferred embodiments, it will be appreciated by those of skill in the art that additions, modifications, substitutions and deletions not specifically described may be made without departing from the spirit and scope of the invention defined in the appended claims.

We claim:

1. A package for a device having a sharp cutting edge, said package comprising a tray having a bottom surface, a top surface and side walls connected between said bottom surface and said top surface, said top surface including an upwardly facing central recessed portion for engaging a device having a sharp cutting edge, said tray defining a downwardly facing recessed area adjacent said central portion, protective means disposed within said downwardly facing recessed area and extending above and below said central portion for preventing a device having a sharp cutting edge from engaging said side walls, said protective means being formed of plastic sponge material which is soft, resilient and tear-resistant, support means for supporting a device having a sharp cutting edge, and retaining means secured to said bottom surface for retaining said protective means and support means in operative position.

2. A package as claimed in claim 1, wherein said downwardly facing recessed area surrounds said central portion.

3. A package as claimed in claim 1, wherein said protective means is complementary in configuration to said recessed area.

4. A package as claimed in claim 1, wherein said support means is surrounded by said protective means.

5. A package as claimed in claim 1, wherein said protective means and said support means are flush with one another on a side of each which faces said retaining means.

6. A package as claimed in claim 1, wherein said tray comprises a transparent plastic material.

7. A package as claimed in claim 1, wherein said tray comprises polyethylene terephthalate.

8. A package as claimed in claim 1, wherein said protective means comprises a polyester foam.

9. A package as claimed in claim 1, wherein said support means comprises a polyester foam.

10. A package as claimed in claim 1, wherein said retaining means comprises a plastic-coated paper material.

11. A package for a device having a sharp cutting edge, said package comprising a tray including a central portion and a recessed area adjacent to the central portion to define an interior space within the tray, a device having a sharp cutting edge disposed within said space in contact with said central portion, protective means disposed within said recessed area for preventing said device from engaging any portion of the tray other than the central portion, said protective means being formed of a plastic sponge material which is soft, resilient and tear-resistant, support means for supporting said device, and retaining means secured to said tray for retaining said protective means and support means in operative position and sealing off said space within said tray.

12. A package as claimed in claim 11, wherein said recessed area surrounds said central portion.

13. A package as claimed in claim 11, wherein said protective means is complementary in configuration to said recessed area.

14. A package as claimed in claim 11, wherein said support means is surrounded by said protective means.

15. A package as claimed in claim 11, wherein said protective means and said support means are flush with one another on a side of each which faces said retaining means.

16. A package as claimed in claim 11, wherein said tray comprises a transparent plastic material.

17. A package as claimed in claim 11, wherein said tray comprises polyethylene terephthalate.

18. A package as claimed in claim 11, wherein said protective means comprises a polyester foam.

19. A package as claimed in claim 11, wherein said support means comprises a polyester foam.

20. A package as claimed in claim 11, wherein said retaining means comprises a plastic-coated paper material.

* * * * *